United States Patent [19]

Masaki

[11] Patent Number: 4,792,777

[45] Date of Patent: Dec. 20, 1988

[54] VARIABLE WATER RESISTOR FOR CONTROLLING THE APPLICATION OF A THERAPEUTIC VOLTAGE TO THE HUMAN BODY

[75] Inventor: Kazumi Masaki, Osaka, Japan

[73] Assignee: Ken Hayachibara, Okayama, Japan

[21] Appl. No.: 89,955

[22] Filed: Aug. 26, 1987

[30] Foreign Application Priority Data

Aug. 31, 1986 [JP] Japan ............................ 61-203954

[51] Int. Cl.[4] ........................................ H01C 10/02
[52] U.S. Cl. ........................................ 338/80; 338/27; 338/94; 338/222; 128/421; 128/422
[58] Field of Search ................ 338/27, 38, 44, 80, 338/94, 222; 128/421, 422; 323/369

[56] References Cited

FOREIGN PATENT DOCUMENTS 51-62582  5/1976  Japan .

Primary Examiner—Patrick R. Salce
Assistant Examiner—Emanuel Todd Voeltz
Attorney, Agent, or Firm—Browdy and Neimark

[57] ABSTRACT

An output controller for low-frequency treatment device for use in a bath, comprising a low-frequency oscillator; a variable water resistor having fixed terminals connected with the output terminal of the low-frequency oscillator; and an active electrode connected with the sliding terminal of the variable water resistor.

3 Claims, 3 Drawing Sheets

FIG.3
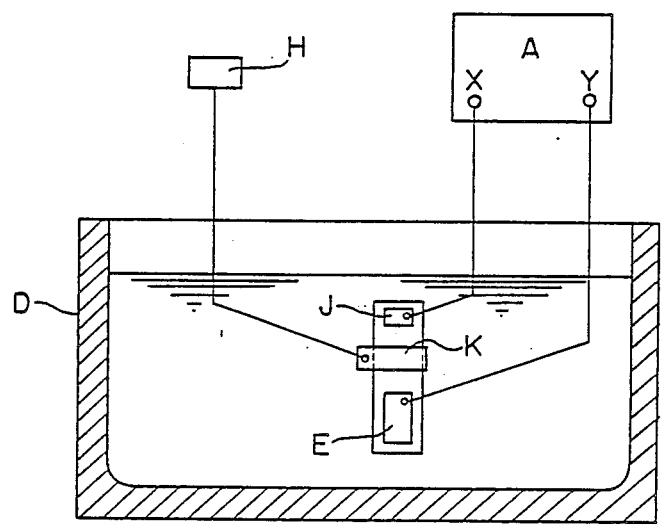
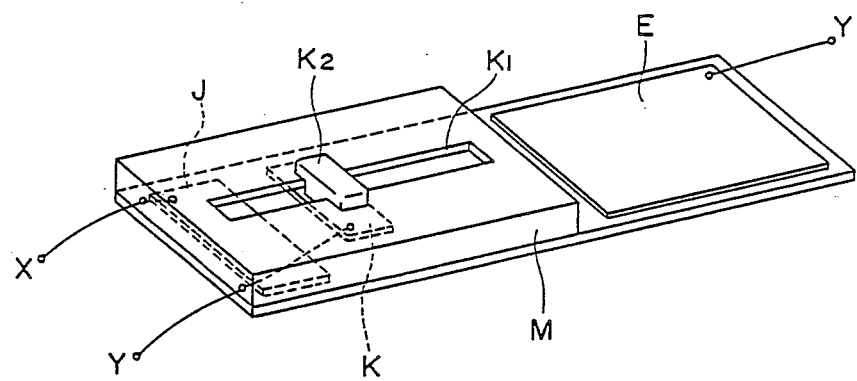
FIG.4

VARIABLE WATER RESISTOR FOR CONTROLLING THE APPLICATION OF A THERAPEUTIC VOLTAGE TO THE HUMAN BODY

BACKGROUND OF THE INVENTION

1. Field of the Invention

The present invention relates to an output controller for low-frequency treatment device directed for use in a bath.

2. Description of the Prior Art

When a low-frequency treatment device is used in a bath, the oscillator and container enclosing the circuit elements must be perfectly water- and moisture-proofed. When the switching mechanism and output controller project outside the container, they are liable to cause troubles.

The present output controller utilizes the electric resistance in bathwater, and the switching mechanism is automatically turned on by placing the output controller in bath-water.

Japanese Patent Laid-Open No. 62,582/76 proposes that a variable resistance is connected in rheostat manner with a load resistance to control the output of a low-frequency oscillator in bathwater. Although this proposal has an economical advantage, it has drawbacks in that it is unsatisfactory in voltage regulation because a resistance is connected in series with the load resistance; as well as in that it causes pain on subject's body when active electrode is put close to it.

SUMMARY OF THE INVENTION

In view of the foregoing, one object of the present invention is to provide an output controller for low-frequency treatment device wherein these drawbacks of conventional device are overcome.

This and other objects as may become apparent hereinafter have been attained with the output controller for low-frequency treatment device for use in a bath, comprising a low-frequency oscillator; a variable water resistor having fixed terminals connected with the output terminal of said low-frequency oscillator; and an active electrode connected with the sliding terminal of said variable water resistor.

BRIEF DESCRIPTION OF THE DRAWINGS

The present invention will hereinafter be described with reference to the accompanying drawings in which:

FIG. 3 is illustrative of the principle of the present invention;

FIG. 4 is the perspective view of a variable water resistor;

DETAILED DESCRIPTION OF THE PREFERRED EMBODIMENTS

Figure 1:
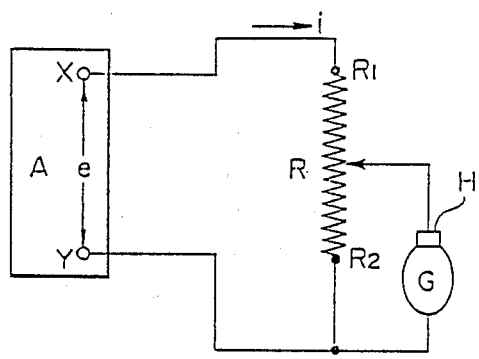
FIG. 1 is the circuit of an embodiment according to the invention.

In the drawings, symbol A designates low-frequency oscillator; B, battery; C, capacitor; D, bathtub; E, earth electrode; G, subject's body; H, active electrode; J, signal electrode; K, sliding electrode; L, transformer; M, insulating cover; R, variable water resistor; and T, transistor.

FIG. 1 is the circuit of an embodiment according to the present invention. In the circuit, when active electrode H is in contact with the subject's body G, the output current "i" from low-frequency oscillator A flows into the subject's body G through active electrode H. The contact resistance is connected in parallel with the resistance between the sliding terminal and terminal $R_2$. The contact resistance usually varies from about one hundred kiloohms, as observed when active electrode H comes close to present subject's body G, to about ten kiloohms as observed when active electrode H is actually placed on the subject's body G. When the output resistance of the variable water resistor is twenty kiloohms and the resistances between the sliding electrode and either of terminals $R_1$ and $R_2$ are equal, the combined resistance with the contact resistance attained when active electrode H comes close to the subject's body G (100 kiloohms) is about nine kiloohms. Thus, the voltage across the contact point on the subject's skin becomes a half of voltage "e" in accordance with the ratio of the combined resistance (nine kiloohms) to the resistance between the sliding terminal and terminal $R_2$ (ten kiloohms). When active electrode H is placed on the subject's body G and the contact resistance decreases to ten kiloohms, the combined resistance of the contact resistance and the resistance between the sliding terminal and terminal $R_2$ becomes five kiloohms, and the voltage across the subject's skin decreases to a third of voltage "e" in accordance with the ratio of the combined resistance to the resistance between terminal $R_1$ and the sliding terminal.

Figure 2:
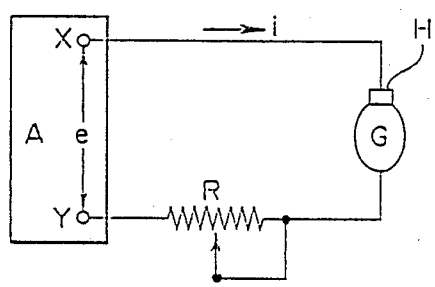
FIG. 2 is the circuit of conventional device.

Referring now to FIG. 2, since in conventional circuit as disclosed in Japanese Patent Laid-Open No. 62,58276 the contact resistance is connected in series with variable water resistor R, when the output resistance is twenty kiloohms and active electrode H comes near to the subject's body G, the voltage across the contact point on the subject's body G is 5/6 of voltage "e" because of the contact residence (100 kiloohms). When active electrode H is actually placed on the subject's body G and the contact resistance decreases to ten kiloohms, the voltage across the contact point on the subject's skin varies to a third of voltage "e". In short, when conventional circuit as shown in FIG. 2 is used, the voltage across the contact point on the subject's body G varies from 5/6 to ⅓ of voltage "e", while with the circuit as shown in FIG. 1 the voltage varies from 1⁄78 to ⅓ of voltage "e". Thus, the present invention is characterized by a decreased voltage variation.

FIG. 3 is illustrative of another embodiment according to the invention. In this embodiment, the output terminal of low-frequency oscillator A is connected with an electrode pair consisting of signal electrode J and earth electrode E. Between the electrode pair, sliding electrode K is provided in such manner that it can be smoothly slide along with the guide plate. Electrodes J, K and E attain a variable water resistor when immersed in water in bathtub D.

FIG. 4 is to explain the principle of the variable water resistor. The fixed electrode pair, i.e. signal electrode J and earth electrode E, is provided on the same plane at an appropriate interval, while sliding electrode K is provided parallel with the electrode pair. Sliding electrode K can be smoothly moved towards signal electrode J and earth electrode E by operating knob $K_2$ along guide slit $K_1$. The closer sliding electrode K comes to signal electrode J, the output voltage becomes higher, while the closer sliding electrode K comes to earth electrode E, the output voltage is nearer to zero.

The surface area of earth electrode E should be enlarged as much as possible in order to reduce the electric resistance in bathwater. The space between the subject's body G and earth electrode E is conductive in bathwater. By covering signal electrode J with insulating material M to minimize its surface area in order to exert an effective surface area only to sliding electrode K, the resistance between signal electrode J and sliding electrode K can be set to several ten kiloohms when sliding electrode K comes near to signal electrode J, while the resistance between signal electrode J and sliding electrode K and that between sliding electrode K and earth electrode E can be set respectively to several ten kiloohms and several ten ohms when sliding electrode K comes near to earth electrode E.

Figure 5:
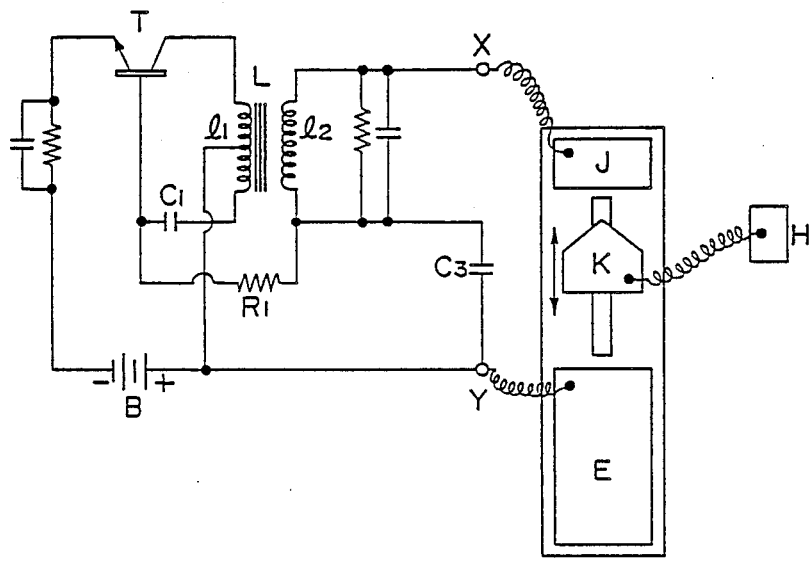
FIG. 5 is an automatic switching circuit.

FIG. 5 is to explain the principle of the automatic switching circuit according to the invention. In the circuit, a blocking oscillator comprising transistor T and transformer L provides a signal having a waveform similar to that of the nervous action potential. When signal electrode J, sliding electrode K and earth electrode E are immersed in bathwater and a variable resistor is attained, the resistance between signal electrode J and earth electrode E is in the range from several kiloohms to several ten kiloohms. The current from battery B flows from its positive terminal through terminal Y to earth electrode E, and the voltage energizes signal electrode J via a water resistance. When it occurs, a positive voltage energizes the base of transistor T from signal electrode J through terminal X, winding $l_2$ and resistor $R_1$ to render transistor T conductive. Thus, blocking oscillation is initiated. The oscillation output is supplied both to earth terminal E from winding $l_2$ through capacitor $C_3$ and terminal Y and to active electrode H from terminal X through signal electrode J and sliding electrode K. Since in bathwater the space between earth electrode E and the subject's body G is kept conductive, a signal current flows from signal electrode K to active electrode H.

Figure 6:
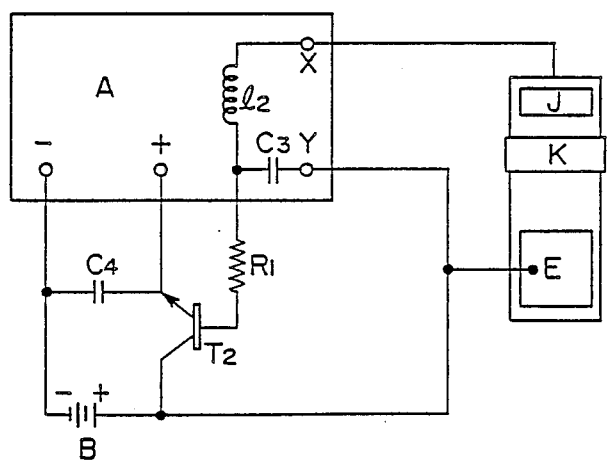
FIG. 6 is another type of automatic switching circuit operable with a relatively small current.

FIG. 6 is illustrative of an automatic switching circuit operable with a relatively small current in water. In this circuit, the power or base biasing source for either low-frequency oscillator A or amplifier is attained with a collector current obtained by operating transistor T with a relatively small current in water. When signal electrode J, sliding electrode K and earth electrode E are immersed in bathwater to attain a variable water resistor, the current from battery B flows from its positive terminal through terminal Y to earth electrode E, and the voltage energizes signal electrode J through a water resistance. The voltage also energizes the base of transistor T from signal electrode J through terminal X, winding $l_2$ and resistor $R_1$. This renders transmissor T conductive, and the positive voltage across the emitter circuit is supplied as the source to low-frequency oscillator A or amplifier circuit.

Since the present invention is arranged in this way, it can supply a stable therapeutic voltage to subject's body and, unlike conventional device, causes no pain during its use.

Since a low-frequency treatment device equipped with the present output controller helps the subject in bathwater to improve the mascular strength and blood circulation, it is advantageously usable to treat hemorrhoids, as well as to relieve fatigue.

Having described specific embodiments of my bearing, it is believed obvious that modifications and variations of my invention are possible in light of the above teaching.

I claim:

1. A variable water resistor for controlling the application of a therapeutic voltage to a human body, comprising:

two fixed electrodes provided at a predetermined interval, said fixed electrodes being connected with an output terminal of a low-frequency oscillator that generates said therapeutic voltage;

a sliding electrode slidable along with said fixed electrodes, said sliding electrode being connected with a therapeutic electrode that is placed on the skin of the human body during therapy; and said fixed electrodes and sliding electrode being soaked in water to form a variable water resistor when in use.

2. The variable water resistor of claim 1, wherein said two fixed electrodes are provided on the same plane with one another and the sliding electrode is provided in parallel with said fixed electrodes.

3. The variable water resistor of claim 1, wherein the variable water resistor is for massage of a subject's body.

* * * * *

UNITED STATES PATENT AND TRADEMARK OFFICE
CERTIFICATE OF CORRECTION

PATENT NO. : 4,792,777
DATED : December 20, 1988
INVENTOR(S) : Kazumi MASAKI

It is certified that error appears in the above-identified patent and that said Letters Patent is hereby corrected as shown below:

On the title page

Correct the name of assignee as follows:

-- [73] Assignee: Ken Hayashibara, Okayama, Japan --

Signed and Sealed this

Sixth Day of June, 1989

Attest:

DONALD J. QUIGG

Attesting Officer

Commissioner of Patents and Trademarks